United States Patent
Wilson et al.

(10) Patent No.: US 11,061,036 B2
(45) Date of Patent: Jul. 13, 2021

(54) METHODS FOR EPITOPE MAPPING

(71) Applicants: Derek James Wilson, King City (CA); Bin Deng, North York (CA); Shaolong Zhu, Toronto (CA)

(72) Inventors: Derek James Wilson, King City (CA); Bin Deng, North York (CA); Shaolong Zhu, Toronto (CA)

(73) Assignees: Derek James Wilson, King City, CA (US); Bin Deng, North York (CA); Shaolong Zhu, Toronto (CA)

( * ) Notice: Subject to any disclaimer, the term of this patent is extended or adjusted under 35 U.S.C. 154(b) by 14 days.

(21) Appl. No.: 16/132,925

(22) Filed: Sep. 17, 2018

(65) Prior Publication Data
US 2019/0086424 A1 Mar. 21, 2019

Related U.S. Application Data

(60) Provisional application No. 62/559,067, filed on Sep. 15, 2017.

(51) Int. Cl.
| | |
|---|---|
| *G01N 33/68* | (2006.01) |
| *G16B 15/30* | (2019.01) |
| *C07K 16/18* | (2006.01) |
| *G16B 20/30* | (2019.01) |
| *G16B 20/00* | (2019.01) |
| *H01J 49/26* | (2006.01) |

(52) U.S. Cl.
CPC ......... *G01N 33/6878* (2013.01); *C07K 16/18* (2013.01); *G01N 33/6848* (2013.01); *G16B 15/30* (2019.02); *G16B 20/00* (2019.02); *G16B 20/30* (2019.02); *G01N 2500/00* (2013.01); *H01J 49/26* (2013.01)

(58) Field of Classification Search
CPC ............... C07K 16/18; G01N 2500/00; G01N 33/6848; G01N 33/6878; H01J 49/26; G16B 15/30; G16B 20/00; G16B 20/30
See application file for complete search history.

(56) References Cited

PUBLICATIONS

"Characterization of Protein Therapeutics," 28th ASMS Sanibel Conference on Mass Spectrometry, Jan. 21-24, 2016, Clearwater Beach, FL, retrieved on Feb. 18, 2020 from https://www.asms.org/docs/default-source/small-conferences-final-programs/2016-sanibel_final-program-web.pdf?sfvrsn=8e3577c3_2, pp. 1-13.*

Wilson et al., "A Capillary Mixer with Adjustable Reaction Chamber Volume for Millisecond Time-Resolved Studies by Electrospray Mass Spectrometry," Anal. Chem., 2003, vol. 75, No. 23, pp. 6408-6414.*

Rob et al., "Measuring Dynamics in Weakly Structured Regions of Proteins Using Microfluidics-Enabled Subsecond H/D Exchange Mass Spectrometry," Anal. Chem., 2012, vol. 84, No. 8, pp. 3771-3779.*

Liuni et al., "A microfluidic reactor for rapid, low-pressure proteolysis with on-chip electrospray ionization," Rapid Commun. Mass Spectrom., 2010, vol. 24, issue 3, pp. 315-320.*

Kwak et al., "Convex Grooves in Staggered Herringbone Mixer Improve Mixing Efficiency of Laminar Flow in Microchannel," PLoS One, 2016; 11(11):e0166068; pp. 1-15; Published online Nov. 4, 2016.*

Deng et al. "Elimination of Allosteric artifacts in Epitope Mapping Experiments using Time-Resolved EleotroSpray Ionization Hydrogen Deuterium Exchange (TRESI-HDX)" presented at "Characterization of Protein Therapeutics," 28th ASMS Sanibel Conference on Mass Spectrometry, Jan. 2016, Clearwater Beach, FL., poster.

\* cited by examiner

*Primary Examiner* — Galina M. Yakovleva
(74) *Attorney, Agent, or Firm* — Myers Bigel, P.A.

(57) ABSTRACT

A TRESI-HDX-based method for mapping protein-protein interactions comprises substantially simultaneously (a) initiating complexation between the proteins and (b) labelling the complex. In aspects, the proteins comprise an antibody and an antigen, an enzyme and a substrate, or a drug and a drug target. In aspects, the labelling time is from about 1 ms to about 1000 ms.

10 Claims, 6 Drawing Sheets

METHODS FOR EPITOPE MAPPING

FIELD

The present invention relates to protein-protein interactions. More specifically, the present invention is, in aspects, concerned with methods for epitope mapping.

BACKGROUND

Epitope mapping is the process of experimentally identifying the binding sites, or 'epitopes', of antibodies on their target antigens. Identification and characterization of the binding sites of antibodies can aid in the discovery and development of new therapeutics, vaccines, and diagnostics. Characterization of epitopes can also help elucidate the mechanism of binding for an antibody and facilitate the prediction of B cell epitopes using robust algorithms. Epitopes can be generally divided into two main classes: linear and conformational. Linear epitopes are formed by a continuous sequence of amino acids in a protein, while conformational epitopes are composed of amino acids that are discontinuous in the protein sequence but are brought together upon three-dimensional protein folding. The vast majority of antigen-antibody interactions rely upon binding to conformational epitopes.

Hydrogen-deuterium exchange (also called H-D or H/D exchange or HDX) is a chemical reaction in which a covalently bonded hydrogen atom is replaced by a deuterium atom, or vice versa. It can be applied most easily to exchangeable protons and deuterons, where such a transformation occurs in the presence of a suitable deuterium source, without any catalyst. The use of acid, base or metal catalysts, coupled with conditions of increased temperature and pressure, can facilitate the exchange of non-exchangeable hydrogen atoms, so long as the substrate is robust to the conditions and reagents employed. This often results in perdeuteration: hydrogen-deuterium exchange of all non-exchangeable hydrogen atoms in a molecule.

H-D exchange has been used to characterize protein structures and protein-protein interactions, such as in epitope mapping. The exchange reaction is carried out with the isolated proteins and with the complex and the exchanging regions are then compared.

There is a need for alternative compositions to overcome or mitigate at least some of the deficiencies of the prior art, or to provide a useful alternative.

SUMMARY

In accordance with an aspect, there is provided a method of mapping protein-protein interactions, the method comprising combining millisecond HDX labelling with on-chip pepsin digestion and electrospray ionization.

In an aspect, the proteins are labeled and the protein-protein complex is formed substantially simultaneously.

In an aspect, the labelling time is from about 1 ms to about 1000 ms.

In an aspect, the labelling time is about 200 ms.

In an aspect, transfer from labeling to ionization is under quench conditions and takes less than about 10 s.

In an aspect, transfer from labeling to ionization takes less than about 4 s.

In an aspect, the method further comprises MS detection and data analysis.

In an aspect, the method is for epitope mapping.

In accordance with an aspect, there is provided a kinetic HDX workflow that suppresses allosteric effects in epitope mapping.

In an aspect, the workflow comprises millisecond HDX labeling followed by acid quenching, digestion, on-chip electrospray ionization, MS detection, and data analysis.

In an aspect, the labelling time is from about 1 ms to about 1000 ms.

In an aspect, the labelling time is about 200 ms.

In an aspect, transfer from labeling to ionization is under quench conditions and takes less than about 10 s.

In an aspect, transfer from labeling to ionization takes less than about 4 s.

In accordance with an aspect, there is provided a method of mapping protein-protein interactions, the method comprising performing millisecond time-resolved electrospray ionization mass spectrometry with hydrogen deuterium exchange (TRESI-HDX) that selectively attenuates or eliminates signals from allosteric effects.

In an aspect, the method selectively attenuates or eliminates signals from allosteric effects by labelling the proteins and forming the protein complex substantially simultaneously.

In an aspect, the labelling time is from about 1 ms to about 1000 ms.

In an aspect, the labelling time is about 200 ms.

In an aspect, transfer from labeling to ionization is under quench conditions and takes less than about 10 s.

In an aspect, transfer from labeling to ionization takes less than about 4 s.

In an aspect, the method further comprises MS detection and data analysis.

In an aspect, the method is for epitope mapping.

In accordance with an aspect, there is provided a method of epitope mapping, wherein the method comprises introducing an antibody to an antigen through a TRESI mixer so that binding and labeling are initiated substantially simultaneously.

In an aspect, the TRESI mixer comprises a TRESI-HDX chip comprising laminar-flow disturbing microstructures after acid-quenching channels for improving mixing between a deuterated protein and a quench solution.

In an aspect, the labelling time is from about 1 ms to about 1000 ms.

In an aspect, the labelling time is about 200 ms.

In an aspect, transfer from labeling to ionization is under quench conditions and takes less than about 10 s.

In an aspect, transfer from labeling to ionization takes less than about 4 s.

In an aspect, the method further comprises MS detection and data analysis.

In accordance with an aspect, there is provided a method of distinguishing between binding and allostery in epitope mapping experiments, the method comprising initiating complexation and HDX labeling simultaneously, thereby allowing for the HDX signal to develop as allostery is propagated after a binding event.

In an aspect, the labelling time is from about 1 ms to about 1000 ms.

In an aspect, the labelling time is about 200 ms.

In an aspect, transfer from labeling to ionization is under quench conditions and takes less than about 10 s.

In an aspect, transfer from labeling to ionization takes less than about 4 s.

In an aspect, the method further comprises MS detection and data analysis.

In accordance with an aspect, there is provided a TRESI-HDX-based method for mapping protein-protein interactions, the method comprising substantially simultaneously (a) initiating complexation between the proteins and (b) labelling the complex.

In an aspect, the proteins comprise an antibody and an antigen, an enzyme and a substrate, or a drug and a drug target.

In an aspect, the labelling time is from about 1 ms to about 1000 ms.

In an aspect, the labelling time is about 200 ms.

In an aspect, transfer from labeling to ionization is under quench conditions and takes less than about 10 s.

In an aspect, transfer from labeling to ionization takes less than about 4 s.

In an aspect, the method further comprises MS detection and data analysis.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which:

FIG. 5. Computational allostery predictions using RTA analysis. (A) Dilution plot of myoglobin (3rgk) using FIRST. The horizontal axis represents the residue numbers and vertical axis the current hydrogen bond energy cutoff in kcal/mol. Flexible regions of the polypeptide chain appear as black thin lines and rigid clusters as coloured blocks. Dash line represent the energy cutoff associated with start of allosteric transmission and long dash line represents the end of allosteric transmission (as shown in C). As hydrogen bonds cutoff is decreased, rigid clusters break up and other parts of the chain become flexible. (B) Rigid clusters mapped onto 3D protein structure at −0.5 kcal/mol. (C) The transmission of conformational degrees of freedom (DOF) from region 112-116 and 140-147 (shown in blue) to region 41-70 (shown in red) (i.e., a change in rigidity at site one propagating to modify rigidity at site two) as a function of energy cutoff. Positive DOF transmission demonstrates the presence of allosteric transmission between the two regions.

DETAILED DESCRIPTION

Described herein are novel methods for mapping protein-protein interactions. These methods are based on TRESI-HDX methods but use very short time periods for labeling and complex formation, typically in the millisecond time range.

The interacting proteins may be any proteins that interact to form a complex. Examples include an antibody and an antigen, an enzyme and a substrate, and a drug and a drug target. Typically, the methods described herein are used in epitope mapping, whereby the interacting proteins are an antibody and an antigen. It will be understood that the entire protein in the native complex is not necessarily required for the methods described herein. For example, an Fab fragment could be used, an scFv could be used, or other such portions or fragments of antibodies and will be understood by a skilled person. Likewise, the entire antigen, enzyme, substrate, drug, or target need not be used in the methods described herein. Portions or fragments may be used provided the portions are sufficiently sized to provide native conformations to the formed complex.

Thus, provided herein is a method of mapping protein-protein interactions, such as an antibody/antigen interaction in epitope mapping, the method comprising combining millisecond HDX labelling with on-chip pepsin digestion and electrospray ionization. Also provided is a method of distinguishing between binding and allostery in protein-protein interaction experiments, the method comprising initiating complexation and HDX labeling simultaneously, thereby allowing for the HDX signal to develop as allostery is propagated after a binding event.

Also provided is a method of mapping protein-protein interactions, the method comprising performing millisecond time-resolved electrospray ionization mass spectrometry with hydrogen deuterium exchange (TRESI-HDX) that selectively attenuates or eliminates signals from allosteric effects. Typically, the method selectively attenuates or eliminates signals from allosteric effects by labelling the proteins and forming the protein complex substantially simultaneously.

Also described herein is a method of mapping protein-protein interactions, wherein the method comprises introducing a pair of complex-forming proteins through a TRESI mixer so that binding and labeling are initiated substantially simultaneously. In aspects, the TRESI mixer comprises a TRESI-HDX chip comprising laminar-flow disturbing microstructures after acid-quenching channels for improving mixing between a deuterated protein and a quench solution.

Also provided herein is a TRESI-HDX-based method for mapping protein-protein interactions, the method comprising substantially simultaneously (a) initiating complexation between the proteins and (b) labelling the complex.

By "substantially simultaneously," it is meant that the labeling of the protein complex and formation of the complex are initiated at approximately the same time. The labeling times for the complexes in the methods described herein are typically less than about 4 seconds, more typically less than about 1 second, such as from about 1 ms to about 1000 ms, such as from about 1 ms, about 10 ms, about 50 ms, about 100 ms, about 150 ms, about 200 ms, about 250 ms, about 300 ms, about 350 ms, about 400 ms, about 450 ms, about 500 ms, about 550 ms, about 600 ms, about 650 ms, about 700 ms, about 750 ms, about 800 ms, about 850 ms, about 900 ms, or about 950 ms to about 10 ms, about 50 ms, about 100 ms, about 150 ms, about 200 ms, about 250 ms, about 300 ms, about 350 ms, about 400 ms, about 450 ms, about 500 ms, about 550 ms, about 600 ms, about 650 ms, about 700 ms, about 750 ms, about 800 ms, about 850 ms, about 900 ms, about 950 ms, or about 1000 ms. Typically, the labeling times are about 200 ms.

Also provided herein is a kinetic HDX workflow that suppresses allosteric effects in epitope mapping. Typically, the workflow comprises millisecond HDX labeling followed by acid quenching, digestion, on-chip electrospray ionization, MS detection, and data analysis.

Typically, transfer from labeling to ionization is under quench conditions and takes less than about 10 s, such as less than about 10 s, about 9 s, about 8 s, about 7 s, about 6 s, about 5 s, about 4 s, about 3 s, about 2 s, or about 1 s. Typically, transfer from labeling to ionization takes less than about 4 s.

For purposes herein, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, Comprehensive Organic Transformations, VCH Publishers, Inc., New York, 1989; Carruthers, *Some Modern Methods of Organic Synthesis*, 3$^{rd}$ Edition, Cambridge University Press, Cambridge, 1987.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation, whether implicitly or explicitly defined herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Suppressing Allostery in Epitope Mapping Experiments Using Millisecond Hydrogen/Deuterium Exchange Mass Spectrometry Abstract A key component of the development of therapeutic monoclonal antibodies is localization of the interface between the candidate antibody and its antigen target, commonly known as epitope mapping. With the recent availability of commercial automated systems, Hydrogen/Deuterium eXchange (HDX) is rapidly becoming a preferred tool for mapping epitopes both in industry and academia. However, this approach has a significant drawback in that it can be confounded by 'allosteric' structural and dynamic changes that result from the interaction but occur far from the point(s) of contact. Here, we introduce a 'kinetic' millisecond HDX workflow that suppresses allosteric effects in epitope mapping experiments. The approach employs a previously introduced microfluidic apparatus that enables millisecond HDX labeling times with on-chip pepsin digestion and electrospray ionization. The 'kinetic' workflow also differs from conventional HDX-based epitope mapping in that the antibody is introduced to the antigen at the onset of HDX labeling. Using myoglobin/anti-myoglobin as a model system, we demonstrate that at short 'kinetic' workflow labeling times (e.g., 200 ms), the HDX signal is already fully developed at the 'true' epitope, but is still largely below the significance threshold at allosteric sites. Identification of the 'true' epitope is supported by computational docking predictions and allostery modeling using the rigidity transmission allostery (RTA) algorithm.

Introduction

Monoclonal antibodies are the largest and fastest-growing class of protein therapeutics in the pharmaceutical industry.[1-5] With this rapidly rising interest has come a need to enhance bioanalytical methods for characterizing mAb structure and activity on the molecular level.[6,7] Techniques that can rapidly map binding epitopes are of particular interest, since this information can guide early-stage protein therapeutic development, provide critical information to support advancement decisions and can ultimately be incorporated into FDA fillings as mechanism of action (MoA) data. For biosimilars, epitope mapping is critical for assessment of bioequivalency. Ultimately, knowledge of a potential mAb drug's epitope can both accelerate development and mitigate risk.

A number of methods have been established for determining epitopes, including X-ray crystallography,[8] nuclear magnetic resonance (NMR) spectroscopy,[9] immunochemical analysis,[10] limited proteolysis,[11] site-directed mutagenesis,[12] computational docking[13] and others. X-ray crystallography and NMR are uniquely powerful, as they can directly provide epitope maps at atomic resolution, however, both also have significant drawbacks. The main issue with X-crystallography is the challenge of producing high quality co-crystals,[14] while NMR suffers from an inherent analyte size limitation that is generally below that of an intact antibody (resulting in the use of FaB fragments to acquire NMR epitope maps).[15] The remaining experimental approaches are lower resolution, susceptible to false positives (and negatives), and tend to be labor intensive:[16]

One emerging technique for epitope mapping is hydrogen/deuterium exchange (HDX) with detection by electrospray ionization mass spectrometry (ESI-MS).[17-22] Briefly, this approach measures the rate at which peptide backbone amide hydrogens are exchanged with deuterium from $D_2O$ solvent.[23-25] The exchange process is structure-sensitive because hydrogen bonding (such as occurs in secondary structure) and solvent access (which depends largely on tertiary structure) attenuate the rate of exchange. Regions with low exchange rates are thus structured and/or solvent inaccessible while regions with high exchange rates are less structured (dynamic) and solvent exposed. In the case of a binding interaction, both new hydrogen bonding contacts and physical blocking of solvent access at the binding site will typically lower deuterium uptake in the 'bound' state compared to the 'unbound state'. In principle, this makes HDX a facile and potentially very powerful approach to map epitopes.[26]

However, a substantial challenge for HDX-based epitope mapping arises from allosteric effects.[27] These effects occur when binding at one site causes a substantial change in conformation or dynamics at a distant site. Since allosteric conformational changes also influence hydrogen bonding and solvent access for backbone amides, they are often indistinguishable from the true binding site in conventional HDX measurements. This is a particular problem for antibody/antigen interactions, where allosteric effects may appear as a discontinuous epitope.

In this work, we introduce a technique based on millisecond time-resolved electrospray ionization mass spectrometry with hydrogen deuterium exchange (TRESI-HDX) that selectively attenuates or eliminates signals from allosteric effects in epitope mapping experiments. TRESI-HDX is analogous to conventional 'bottom-up' HDX experiments (in which the labeled protein is digested using an acid protease prior to analysis), but uses millisecond time-scale deuterium labeling, which allows for investigations on rapid conformational changes,[28] weak binding interactions[29] and intrinsically disordered proteins.[30,31] The experiment also differs from conventional epitope mapping in that the antibody is not pre-incubated with the antigen, but is instead introduced to the antigen concomitantly with $D_2O$ solvent so that binding and labeling occur simultaneously. The result is a method that combines aspects of continuous and pulsed HDX labeling, allowing the development of allostery shortly after binding influence the evolution of the deuterium uptake profile. Because conformational equilibria are not fully established at early (millisecond) labeling timepoints, we call this approach 'kinetic' HDX labeling. Using myoglobin/anti-myoglobin as a model system, we find that with 'kinetic' HDX, allosteric effects are specifically suppressed for the first roughly 200 ms of HDX labeling, allowing for higher-confidence determination of the 'true' epitope.

Materials and Methods

Materials

Human myoglobin (ab96036, ~17 KDa) and anti-myoglobin monoclonal antibody (ab19607, ~150 KDa) were purchased from Abcam (Cambridge, Mass., USA). Pepsin (P6887), ubiquitin (U6253), deuterium oxide ($D_2O$, 99.9%, 151882) and high purity acetic acid (>99.7%, 695092) were purchased from Sigma-Aldrich (St. Louis, Mo.). Endoproteinase GluC (P8100S) was purchased from New England Biolabs (Hitchin, UK). Agarose resin (NHS-activated, 26196) was purchased from Thermo Scientific (Rockford, Ill.). HPLC-grade ammonium acetate, acetonitrile, methanol, water and methyl yellow (151400250) were purchased from Fisher Chemical (Fair Lawn, N.J.).

Native Gel Separation of the Myo-mAb Complex

The binding complex of myoglobin and anti-myo mAb was separated by native polyacrylamide gel electrophoresis (PAGE) following the protocol from the Institute of Molecular Development LLC (http://www.molecularinfo.com/). 10 μL of proteins (1.7 μg) and complex (15 μg) samples were loaded in each lane and a voltage of 120 volts was applied for 100 min. The results were indicated by Coomassie brilliant blue R250 staining and photos were taken by Alphalmager HP imaging system (Alpha, San Jose, Calif.).

Size Exclusive Chromatography-MS (SEC-MS) of the Myo-mAb Complex

20 μL of 10 μM myoglobin, anti-myo mAb, and myoglobin-antibody complex with ubiquitin as the internal standard were characterized by using an Agilent 1200 HPLC (Santa Clara, Calif.) with BioSep-SEC-S4000 column (5 μm, 300×7.8 mm, Phenomenex, Torrance, Calif.) coupled with the Synapt G1 HDMS (Waters, Milford, Mass.). The mobile phase was 200 mM ammonium acetate (pH 7.4) with a flow rate of 0.2 mL/min. Data was collected and analyzed using Waters MassLynx 4.1 software.

Microfluidic Chip Fabrication for HDX-MS

The chip device was fabricated on a rectangular piece of poly(methyl methacrylate) (PMMA) with dimensions of 8.9 cm×3.7 cm×0.5 cm. The micro-channels, microstructures, and digestion well within the chip were designed using CoreIDRAW X3 software (Ottawa, ON) and were engraved on PMMA using the VersaLaser (Universal Laser Systems, Scottsdale, Ariz.). The solutions were driven by syringes (Hamilton, Reno, Nev.) on infusion pumps (Harvard, Holliston, Mass.).

For HDX labeling, the TRESI apparatus was assembled as described previously.[31,32] Briefly, a polyimide coated fused silica capillary (I.D. 75 µm, O.D. 150 µm, Polymicro, Pheonix, Ariz.) was inserted into a stainless metal capillary (I.D. 178 µm, O.D. 356 µm, McMaster-Carr, Aurora, Ohio) via a three-way PEEK union (IDEX, Lake Forest, Ill.). Mixing of the two solutions occurred within the intercapillary space when the solution was released from a notch cut 2 mm from the sealed inner capillary end. HDX profiles were acquired by steadily pulling back the inner capillary to increase the reaction volume that resulted in the increase of the labeling times. Under these conditions, back exchange has been shown to be negligible (<5%) due to the rapid (<4 s) transfer from labeling to ionization under quench conditions.[31]

TRHDX-MS for Equilibrium and Kinetic Epitopes

Proteins were desalted before MS detection by buffer exchange with 200 mM ammonium acetate (pH 7.0) using Zeba Spin Desalting columns (89890, 7K, Thermo) on Allegra 25R centrifuge (Beckman, Mississauga, ON) by centrifugation at 1000 g/min at 4° C.

In the equilibrium workflow, 10 µM myoglobin was incubated with 10 µM anti-myo mAb in 200 mM ammonium acetate (pH 7.4) for 30 min at room temperature. The myoglobin-antibody complex was then labeled with $D_2O$ in the TRESI device from 0.20 s to 3.92 s. The HDX reaction was quenched in the chip by rapidly mixing with 5% acetic acid of pH 2.5. The binding complex was then digested by pepsin-linked agarose resin in the digestion well on the chip. The peptides were electrosprayed into a QStar Elite Qq-TOF mass speCtrometer (AB Sciex, Concord, ON). The MS data was analyzed using AB Sciex Analyst 2.0 software. By comparison between the equilibrium complex and native myoglobin, the regions of antibody-bound myoglobin showing significantly less $D_2O$ uptake were identified as equilibrium epitopes.

In the kinetic workflow, the mAb was initially incubated with excess $D_2O$ for 30 min at room temperature. The deuterated antibody was then mixed with myoglobin at the same labeling times from 0.20 s to 3.92 s. The myo-mAb complex was kinetically formed while the $D_2O$ labeling was initiated. Similarly, HDX was stopped by acid quenching, followed by protease digestion and MS detection. Kinetic epitopes were recognized by comparison between the kinetically formed myo-mAb complex and native myoglobin. The regions showing significantly less exchange were identified as kinetic epitopes.

HDX Data Analysis

The peptides from the digested myoglobin were screened using FindPept on the ExPASy Server (Swiss Institute of Bioinformatics, Basel, Switzerland). Deuterium uptake of each peptide was calculated using an in-house written FORTRAN software for isotopic distribution analysis and was normalized to the maximum $D_2O$ uptake of 50%. HDX on myoglobin structures were rendered using PyMOL 1.8 software.

Digestion of the Anti-Myo mAb

Dual-protease digestion was carried out to map peptides of the anti-myo mAb. 20 µL of 15 µM anti-myo mAb was reduced with 20 mM dithiothreitol (DTT) in 0.5 M Tris-HCl (pH 8.0) for 60 min at 37° C. After that, the antibody was alkylated with 10 mg/mL iodoacetamide (1/1, v/v) in 10 mM ammonium bicarbonate at room temperature for 10 min in the dark. Then the sample was treated with 0.1 mg/mL trypsin with a 20:1 protein:protease w/w ratio at 37° C. overnight. For further digestion, the sample was added to 0.1 mg/mL Glu-C with a 40:1 protein:protease w/w ratio at 37° C. for an additional 2 hours. The enzymatic activity was quenched by adding 1 µL 10% acetic acid. The digested anti-myo mAb peptides were desalted using C18 ZipTip pipette tips (EMD Millipore, Etobicoke, ON) prior to LC-MS analysis. Briefly, ZipTips were cleaned with acetonitrile and equilibrated with water. The sample was bound to the ZipTips and washed with 0.1% formic acid in water. The peptides were eluted using 20 µL of 80% acetonitrile, dried using a speed vacuum centrifuge, and reconstituted in 0.1% formic acid.

LC-MS/MS for Antibody Peptide Mapping

The peptides were separated by reversed-phase chromatography using an Agilent 1200 HPLC with Aeris Peptide XB-C18 column (Phenomenex) (3.6 µm, 150×4.6 mm) coupled with Waters Synapt G1 HDMS or Thermo Orbitrap Elite MS (Thermo, Waltham, Mass.). Samples were loaded onto the column using a loading buffer composition of 5% acetonitrile (ACN) and 0.1% formic acid (FA) at a flow rate of 200 µL/min for 15 min. The acetonitrile composition was linearly increased to 100% in 80 min followed by a column re-equilibration step for 30 min. The LC-MS/MS data were processed using Waters PLGS 3.0 software or using Thermo Proteome Discoverer 1.4 software. The data were matched to a Mus musculus database (Uniprot, Apr. 20, 2016) with the addition of porcine trypsin and common human contaminants using a 10 ppm mass accuracy threshold, the oxidation of methionine residues as a variable modification and the carbamidomethylation of cysteine residues as a fixed modification. The protein matches were processed with a 1% false-discovery rate and a 99% peptide confidence cutoff.

Computational Docking

The structure of myoglobin was extracted and modified from the crystal structure of human myoglobin (PDB code: 3RGK). Based on the segments of antibody structure, the structures of four peptides from anti-myo mAb were generated with Molecular Operating Environment (MOE) 2013.08,[47] respectively. Three approaches, ZDOCK,[48] PatchDock[49] and MOE, were utilized to dock myoglobin with the four peptides. In the docking, the modes with or without HDX-MS constraints were both applied. In docking without HDX-MS constraints, there was no constraint for all the three software, where the docking results were only dependent upon the docking algorithms. While in docking with HDX-MS constraints, the epitope residues of I112-L116 and R140-Y147 of myoglobin were set as the docking sites in PatchDock and MOE and as volume constraint pharmacophores in MOE. In ZDOCK, non-epitope residues of myoglobin were blocked as a scoring penalty.

Computational Allostery Prediction

Starting with a crystal structure of myoglobin (pdb id: 3rgk), missing hydrogen atoms were added using the WHAT IF web server (http://swift.cmbi.ru.nl/servers/html/htopo.html). FIRST was run as previously described.[38] FIRST generates a constraint network consisting of nodes (atoms) and edges (e.g. constraints representing covalent bonds, hydrogen bonds, hydrophobic and electrostatic interactions). Each potential hydrogen bond is assigned an energy strength dependent on donor-hydrogen acceptor geometry (reference), and hydrogen bond energy cutoff value is selected where all bonds weaker than this cutoff are ignored in the network. The resulting protein network is then decomposed into rigid clusters and flexible regions. The patterns of rigidity loss during progressive removal of hydrogen bonds is visualized on 'dilution plot' (see FIG. 5A).[38] For dilution, FIRST performs rigidity analysis with all potential hydrogen bonds of energies 0 kcal/mol or lower. Hydrogen bonds are then removed in order of increasing strength gradually reducing the rigidity of the structure. Rigidity calculation over the main-chain and side-chain and rigid cluster decomposition is performed every time a hydrogen bond is removed from the list of constraints.

Once the output of FIRST rigid cluster decomposition is generated, to probe the allosteric transmission between regions 112-16, 140-147 and region 41-70, the rigidity-transmission allostery (RTA) algorithm is applied.[39] The number of conformational degrees of freedom at 41-70 region was calculated before and after perturbation of rigidity of 112-116 and 140-147, and subsequent degree of freedom transmission is obtained as a function of hydrogen bond energy cutoff as described in ref.[39] Positive degree of freedom transmission indicates presence of rigidity-based allostery.

Results

Microfluidics-Enabled TRESI-HDX

Figure 1:
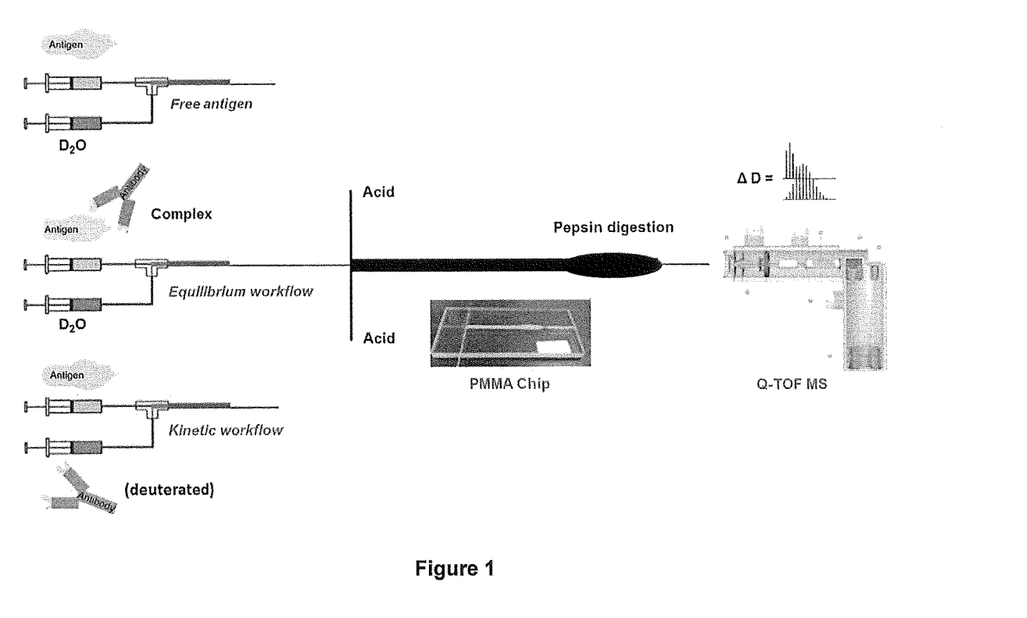
FIG. 1. Schematic of the three TRESI-HDX experiments carried out in this work. All three workflows incorporate millisecond HDX labeling followed by acid quenching, digestion, on-chip electrospray ionization, MS detection and data analysis. (Top) TRESI-HDX of free antibody. Peptide-specific uptake data from this experiment are subtracted from 'equilibrium' or 'kinetic' experiment data to provide HDX difference profiles associated with complexation. (Middle) 'Equilibrium' workflow: Antibody and antigen are pre-equilibrated prior to analysis. (Bottom) 'Kinetic' workflow: Antibody is introduced to the antigen through the TRESI mixer, so that binding and labeling are initiated simultaneously.

A schematic of TRESI-HDX apparatus and workflow is shown in FIG. 1. Millisecond hydrogen-deuterium exchange occurs in the concentric capillary TRESI mixer that is incorporated into a PMMA microfluidic chip as described previously.[31,32] In this implementation of the TRESI-HDX chip, laminar-flow disturbing microstructures were included after the acid quenching chanels to improve the mixing between the deuterated protein and the quench solution. The efficient mixing with acetic acid (pH 2.5) and rapid transfer from the labeling step through pepsin digestion to ionization, allows this setup to largely avoid back exchange, which is often a significant problem in conventional bottom up HDX systems, particularly when LC separation is incorporated.[23,33]

Characterization of the Mb:Anti-Mb Complex by Native-PAGE and SEC-MS

Figure 2:
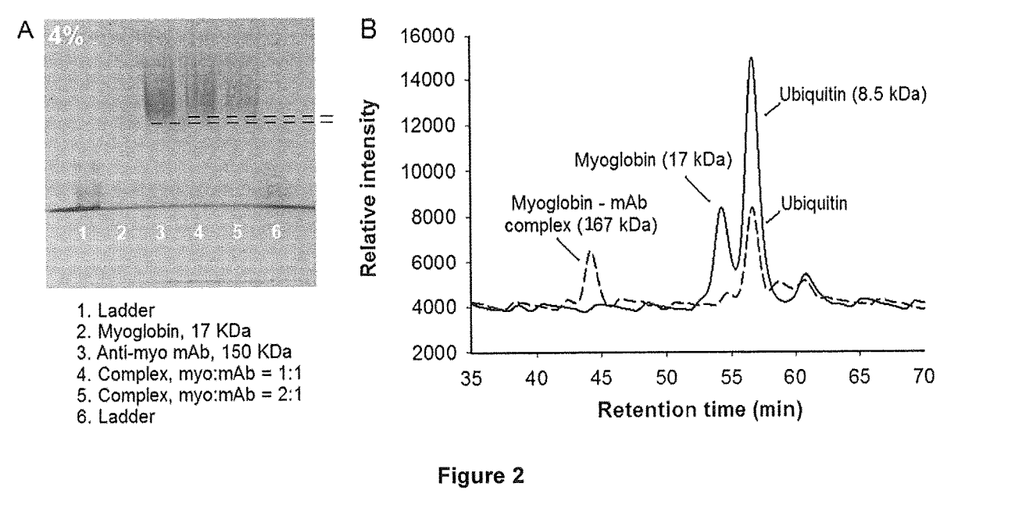
FIG. 2. Detection of the Mb:anti-Mb complex. (A) Mb:anti-Mb complexation is detectable in native-PAGE as a slight retardation of migration (lanes 4 and 5) compared to the free antibody (lane 3). (B) SEC-MS chromatograms showing the elution of myoglobin in the absence and presence of anti-MB (solid line and dashed line, respectively). Ubiquitin was used as an internal standard.

To confirm the formation of the Mb:anti-Mb complex, native polyacrylamide gel electrophoresis (PAGE) and size exclusion chromatography (SEC)-MS were used. In the native-PAGE gels (FIG. 2A), a slight retardation was observed for the bound complex (myo-mAb, 167 KDa, lanes 4 and 5) compared to the free antibody (150 kDa, lane 3), which is consistent based on the small size increase. Under the same conditions, myoglobin (17 KDa, lane 2) had migrated off of the gel. SEC-MS provided a more definitive picture of complexation. The SEC-MS total ion current (TIC) chromatograms are shown in FIG. 2B. Ubiquitin (8.5 kDa), the internal standard, eluted at the same time (56.6±0.1 min) for all runs. Without anti-Mb, Mb (17 kDa) eluted at 54.2±0.1 min. Upon addition of anti-Mb, the Mb signal was detected exclusively at 44.3±0.2 min, indicating complete complexation, which is expected for the concentrations used ($K_D$=1.78 nM).[34]

Equilibrium Epitope Mapping

For equilibrium epitope mapping experiments, anti-Mb was pre-incubated with Mb in a 1:1 ratio (10 µM) and allowed to equilibrate for 30 mins at room temperature. Once the complex was fully equilibrated, the solution was transferred into the microfluidic device for millisecond timescale HDX labeling, quench, digestion and online MS analysis of the resulting peptides. Peptides from Mb were identified by MS/MS and their deuterium uptake levels were calculated using an in-house built program as described previously.[31] When anti-Mb was present, peptides from the mAb were observed, but coverage was insufficient to directly identify the paratope via HDX. This is likely due to inefficient digestion by pepsin due to the presence of disulfides. A putative paratope was ultimately determined by docking hyper-variable region peptides to the epitope determined below (see subsequent sections).

Figure 3:
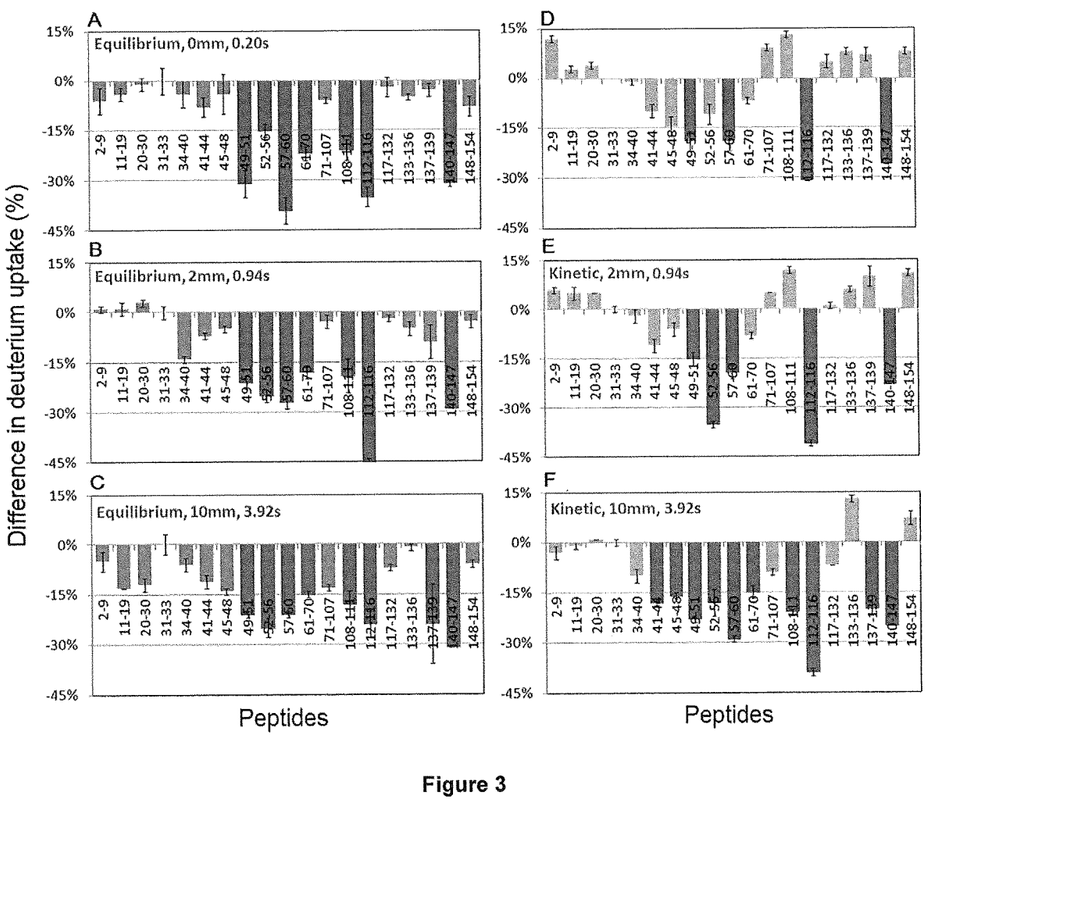
FIG. 3. Differences in deuterium uptake (%) between myoglobin-antibody complex and native myoglobin at different reaction times detected by TRHDX-MS. X-axis shows the sequence of the localized peptides. (A-C) Equilibrium workflow: Mb pre-incubated with anti-Mb for 30 minutes prior to HDX-MS analysis. (D-F) Kinetic workflow: Mb was introduced to anti-Mb antibody concomitantly with the onset of labeling in the TRESI mixer.

In HDX experiments, peptic digestion of Mb resulted in 98% coverage of the myoglobin sequence with an average segment length of 6 residues. The results of epitope mapping on the equilibrium binding complex are shown in FIG. 3 (left column), which plots the deuterium uptake difference between the Mb:anti-Mb complex and free Mb (i.e., $HDX_{mb:anti-Mb}$-$HDX_{Mb}$). For the vast majority of peptides, HDX decreased upon complexation, resulting in negative difference values. Using the average change in uptake (15%) as a significance threshold, regions corresponding to 49-70, 108-116, and 140-147 showed an above-average effect and might tentatively be assigned as corresponding to an epitope. As expected, these results were essentially independent of labeling time, although most regions showed a subtle difference increase over time, which can be attributed to widespread, subtle changes in dynamics upon binding (the subtler the change in HDX accessibility, the longer it takes to 'develop' in the HDX difference plot).

The identified regions agreed quite well with the closest matching epitopes from literature, which reported regions of 15-21, 56-62, 94-100, 113-119, 146-151 on myoglobin.[35] However, these results were obtained for sperm-whale myoglobin using a polyclonal system and a pepscan approach. To the best of our knowledge, our study is the first to provide epitope information for human myoglobin interacting with a mouse mAb.

Kinetic Epitope Mapping

The results of the kinetic experiment (described schematically in FIG. 1) are shown in FIG. 3 (right column). At the earliest mixing time of 0.20 s, a 15% difference threshold identifies regions 49-51, 57-60, 112-116, and 140-147, with substantially weaker attenuated uptake in the 49-70 region compared to the equilibrium measurement. Decreases in the 112-116 and 140-147 regions, however, are similar in magnitude to those observed in the equilibrium data. In contrast to the equilibrium experiment, the kinetic experiment profile changes over time, with uptake differences 'building in' to ultimately produce a profile that is similar to the equilibrium one after only a few hundred ms of labeling. At 3.92 s, the equilibrium and kinetic profiles are similar enough that they generate essentially identical epitope maps when the 'greater than average' 15% cutoff is used, identifying 41-70, 108-116, and 137-147 as potential epitopes.

One interesting feature of the 'kinetic' data is the occurrence of relatively faster uptake in some regions shortly after binding. These effects, while not above the 'hit' threshold in magnitude, are nonetheless statistically significant and sometimes persistent over the timescale of the measurements, particularly for the short segments 133-136 and 148-154. Similar increases have been detected previously in the context of ligand binding in HDX pulse labeling experiments[36] and may reflect slow rearrangement of the target protein conformational ensemble to the 'bound configuration' after binding.

Peptide Mapping of Antibody

LC-MS was applied to identify peptides for possible complementary determining regions (CDRs) on the antibody. The anti-myo mAb was digested with trypsin and Glu-C proteases. The resultant peptides were separated by LC-MS and matched to a Mus musculus database. Based on matched peptides, 76% of the secreted form of IgG-1 chain C region sequence was covered. After filtering for common contaminants, 4 peptides were identified that were correctly sequenced, but did not match the Mus musculus database. Specifically, these peptides were: Peptide 1—mouse IgG1 hypervariable region (Ighv1-62-2) [Uniprot: A0A075B680]; peptide 2—mouse Ig heavy chain V region [Uniprot: P01741]; peptide 3—mouse Ighv1-77 [Uniprot: A0A0B4J1M0]; peptide 4—mouse Igkv14-100 [Uniprot: A0A075B5K7]. These peptides were submitted for epitope-constrained docking simulations to determine if they may correspond the anti-Mb paratope.

Docking Simulations

Docking simulations were carried out using the PatchDock, ZDOCK and MOE software packages. Ten MD-minimized docking poses were evaluated for PatchDock and ZDOCK, while five poses were selected from MOE. Simulations were carried out either with no constraints or with 'site specified' bias or volume constraints based on the HDX data. Optimal poses were determined by measuring the number of energetically favorable contacts between the peptide and Mb. A residue would be regarded as a 'hit' when it was one of the 13 HDX-predicted epitope residues on myoglobin and located within 4.5 Å of a residue from the antibody peptide.

Figure 4:
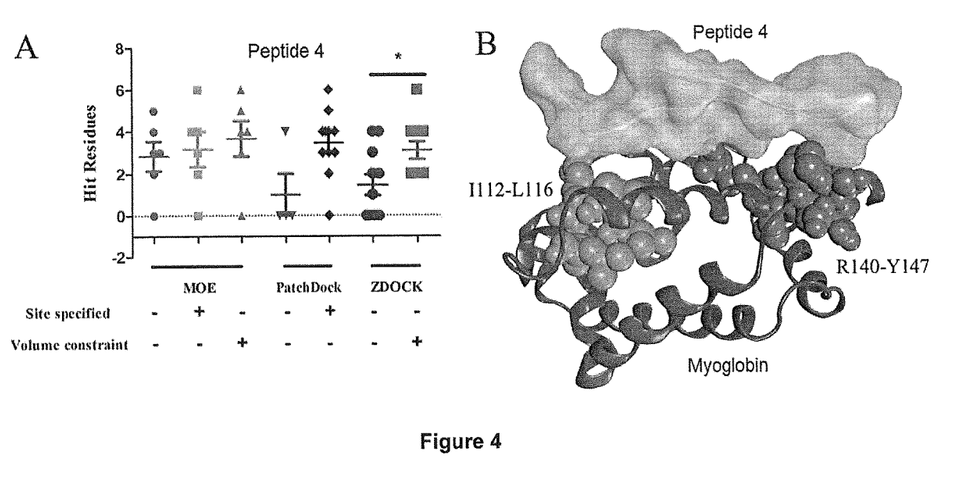
FIG. 4. Computational docking on myoglobin with the peptides from the anti-myo mAb. The software of MOE, PatchDock, and ZDOCK were used to generate the binding models. (A) The peptide 4 (Uniprot: A0A075B5K7) showed a significant difference in docking with and without HDX constraints by using ZDOCK and (B) the binding model of the peptide 4 with myoglobin.

The results showed that for all three software packages, computational docking with HDX-MS constraints produced more hit residues than docking without HDX-MS constraints. Similarly, more 'hit' residues were detected for docking at the HDX-specified site compared to randomly selected sites. In 3D-modeling of the optimal poses for peptides 1-3, however, it quickly became evident that these peptides could only recognize the putative epitope region I112-L116 on myoglobin i.e., they were simply not large enough to create a discontinuous epitope for any pair of sites identified by HDX and they lacked specificity for the other two sites. On the other hand, peptide 4 showed recognition to two identified regions corresponding to I112-L116 and R140-Y147 on myoglobin. Therefore, peptide 4 was chosen to generate a predicted binding complex model as shown in FIG. 4. The other site identified in equilibrium and longer-labeling kinetic experiments (49-70) is located on the opposite face of Mb and showed substantially lower scores for all peptides.

Computational Predictions of Allostery

To probe the presence of allosteric effects, we applied the rigidity-transmission allostery (RTA) algorithm which can assess the extent to which binding events at one site on the protein allosterically influence remote regions. RTA analysis, which utilizes rigidity theory[37] and the FIRST computational method[38], predicts the extent to which local mechanical perturbation of rigidity (mimicking ligand binding) at one region can transmit across a protein structure and cause a change in rigidity and conformational degrees of freedom at a second distant region. RTA has been shown to effectively capture allosteric effects in various protein structures, including enzymes and membrane receptors.[39]

Figure 5:
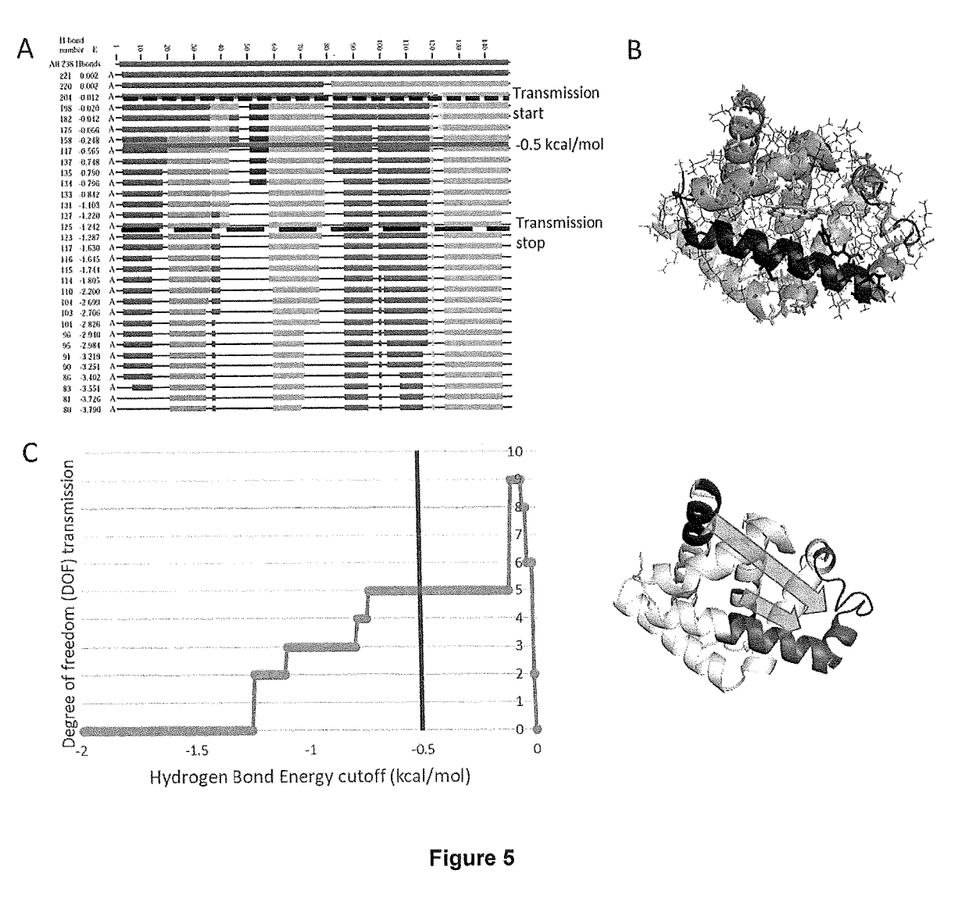

As discussed in method section, we first used the FIRST program to decompose the myoglobin structure into flexible and rigid regions (FIG. 5A, B) and then applied the RTA algorithm to evaluate if perturbation of rigidity in regions 112-116 and 140-147 causes changes in rigidity and conformational degrees of freedom in 41-70 (FIG. 5C). The RTA algorithm calculates the available conformational degrees of freedom at residues 41-70 before and after perturbation of rigidity in the 112-116 and 140-147 regions. In this way, any subsequent change in conformational degrees of freedom due to the initial perturbation is obtained. Mechanically, the presence of rigidity-based allostery (positive degree of freedom transmission) means that a change in shape or rigidity at one site will lead to a change in shape and/or rigidity at the second site.

Binding events at residues 112-116 and 140-147 introduce new local constraints, and RTA analysis shows that this initial perturbation of rigidity results in a change in the available degrees of freedom specifically in the 41-70 region (FIG. 5C), hence computationally demonstrating that allosteric transmission propagates between the two sites. Perturbation of rigidity of both 112-116 and 140-147 regions is required to observe the observed allosteric effect in 41-70 region, however the RTA analysis predicts allosteric transmission is slightly more dependent on the binding events in 112-116 region (data not shown). Furthermore, allosteric transmission persists for a wide range of energy cutoffs indicating 'robust' allosteric communication, meaning small changes in the hydrogen bonding network (e.g. hydrogen bond flickering) will likely not significantly affect the allosteric transmission.

Discussion

Kinetic vs Equilibrium Epitope Mapping

Figure 6:
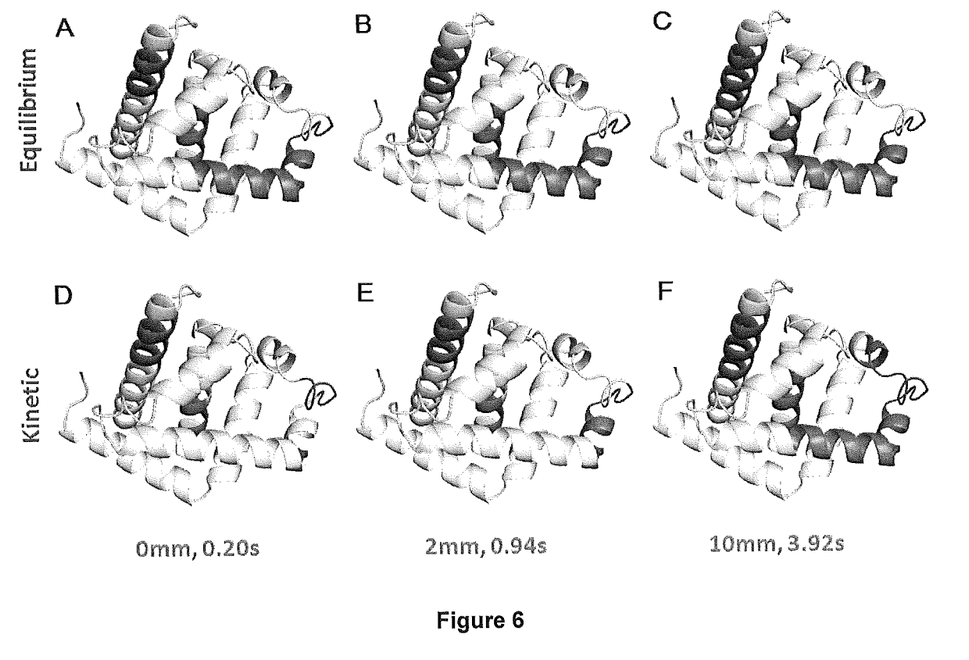
FIG. 6. Epitopes on human myoglobin were indicated as blue regions on its 3D structures. The binding complexes were obtained by both equilibrium (A-C) and kinetic (D-F) workflows with TRHDX-MS detection at different $D_2O$ labeling time (0.20, 0.94 and 3.92 s). Figures were drawn using PyMOL software. Compared to the equilibrium workflow, the kinetic workflow can clearly show the dynamics of conformational changes on myoglobin during the mAb binding process on a sub-second time scale.

In this work, two epitope mapping workflows of TRESI-HDX, 'equilibrium' and 'kinetic', were compared using human myoglobin with monoclonal mouse anti-Mb as a model. Based on a 'greater than average decrease' criterion, peptide regions with over 15% decrease in deuterium uptake were selected as potential epitopes. The epitopes identified by each workflow at different $D_2O$ labeling times (0.20, 0.94 and 3.92 s) are highlighted as blue regions on the myoglobin 3D structures in the FIG. 6.

It is clear from this representation of the data that the kinetic workflow ultimately produced similar epitope predictions (namely 49-70, 108-116, and 137-147) to the equilibrium workflow. The essential difference is that, while the equilibrium workflow generated an unchanging profile as a function of labeling time (FIG. 6A-C), short interaction time profiles from the kinetic experiment exhibit a substantial bias towards the 108-116 and 137-147 regions (FIG. 6D). The detection of transient conformational changes in mAb:target binding, could be critical for the understanding of the mechanism and physiological consequences of a wide array of antibody:antigen interactions. The same workflow can be applied for investigating other antigens and antibodies, as well as other types of interactions, such as enzyme-substrate and drug-target reactions.

Suppression of Allosteric Effects in Epitope Mapping

Allosteric effects, which involve conformational or dynamic changes remote from the active (or binding) site[40] are critical to a wide array of protein functions.[27,41] However, in an epitope mapping experiment, allosteric effects are essentially false positives.[16] In conventional HDX-MS epitope mapping (with 10 s to multiple hours labeling times) and even for the TRESI-MS 'equilibrium' experiments conducted here, pre-incubation for extended periods ensures not only that complexation is equilibrated, but also that allosteric effects have had orders of magnitude more time than needed to fully develop prior to analysis. In the 'kinetic' workflow demonstrated here, complexation and HDX labeling are initiated simultaneously, which allows for the HDX signal to develop as allostery is propagated after a binding event. The result is a novel molecular probe of allosteric propagation with a critical capability, at least in the system studied here, of helping to distinguish between binding and allostery in epitope mapping experiments.

While the results of the 'kinetic' workflow experiment are unambiguous and reproducible, it is difficult to connect what we observe—the development of an 'allosteric' HDX signature over a period of milliseconds—to what is commonly understood about the biophysics of allostery from other measurements. Computational predictions in particular suggest that the transmission of conformational changes associated with allostery should occur on the ns-low µs timescale.[42,43] Nonetheless, a handful of studies have reported substantially slower allosteric effects in small proteins,[44] including pulse-labeling experiments from our group,[36] and the occurrence of allosteric conformational changes on the seconds timescale has long been established in large (usually transmembrane) systems.[45,46]

Exploration of the physical basis of the slow (ms) allostery we report here, as well as the application of the 'kinetic' workflow to trace allosteric pathways in other systems like enzymes and non-antibody protein complexes are clear avenues for further work. In the present work, we have shown that millisecond HDX using the 'kinetic' workflow provides a path to HDX-based epitope mapping experiments in which allosteric effects are selectively suppressed. This would represent a substantial improvement for a technique that is rapidly being adopted both in academic and industrial research.

REFERENCES

1. Buss N A P S, Henderson S J, McFarlane M, Shenton J M, de Haan L. Monoclonal antibody therapeutics: history and future. Curr Opin Pharmacol 2012; 12:615-22.
2. Rodgers K R, Chou R C. Therapeutic monoclonal antibodies and derivatives: Historical perspectives and future directions. Biotechnol Adv 2016; 34:1149-58.
3. Chan A C, Carter P J. Therapeutic antibodies for autoimmunity and inflammation. Nat Rev Immunol 2010; 10:301-16.
4. Weiner L M, Surana R, Wang S. Monoclonal antibodies: versatile platforms for cancer immunotherapy. Nat Rev Immunol 2010; 10:317-27.
5. Walsh G. Biopharmaceutical benchmarks 2014. Nat Biotechnol 2014; 32:992-1000.
6. Barlow D J, Edwards M S, Thornton J M. Continuous and discontinuous protein antigenic determinants. Nature 1986; 322:747-8.
7. Gershoni J M, Roitburd-Berman A, Siman-Tov D D, Tarnovitski Freund N, Weiss Y. Epitope mapping: the first step in developing epitope-based vaccines. BioDrugs Clin Immunother Biopharm Gene Ther 2007; 21:145-56.
8. Chen E, Salinas N D, Huang Y, Ntumngia F, Plasencia M D, Gross M L, Adams J H, Tolia N H. Broadly neutralizing epitopes in the Plasmodium vivax vaccine candidate Duffy Binding Protein. Proc Natl Acad Sci USA 2016; 113:6277-82.
9. Bardelli M, Livoti E, Simonelli L, Pedotti M, Moraes A, Valente A P, Varani L. Epitope mapping by solution NMR spectroscopy. J Mol Recognit JMR 2015; 28:393-400.
10. Atassi M Z. Antigenic structure of myoglobin: the complete immunochemical anatomy of a protein and conclusions relating to antigenic structures of proteins. Immunochemistry 1975; 12:423-38.
11. Suckau D, Köhl J, Karwath G, Schneider K, Casaretto M, Bitter-Suermann D, Przybylski M. Molecular epitope identification by limited proteolysis of an immobilized antigen-antibody complex and mass spectrometric peptide mapping. Proc Natl Acad Sci USA 1990; 87:9848-52.
12. Benjamin null, Perdue null. Site-Directed Mutagenesis in Epitope Mapping. Methods San Diego Calif. 1996; 9:508-15.
13. Grellier B, Le Pogam F, Vitorino M, Starck J-P, Geist M, Duong V, Haegel H, Menguy T, Bonnefoy J-Y, Marchand J-B, et al. 3D modeling and characterization of the human CD115 monoclonal antibody H27K15 epitope and design of a chimeric CD115 target. mAbs 2014; 6:533-46.
14. Dyson H J, Wright P E. Intrinsically unstructured proteins and their functions. Nat Rev Mol Cell Biol 2005; 6:197-208.
15. Frueh D P, Goodrich A C, Mishra S H, Nichols S R. NMR methods for structural studies of large monomeric and multimeric proteins. Curr Opin Struct Biol 2013; 23:734-9.
16. Pandit D, Tuske S J, Coales S J, E S Y, Liu A, Lee J E, Morrow J A, Nemeth J F, Hamuro Y. Mapping of discontinuous conformational epitopes by amide hydrogen/deuterium exchange mass spectrometry and computational docking. J Mol Recognit JMR 2012; 25:114-24.
17. Zhang H, Cui W, Gross M L. Mass spectrometry for the biophysical characterization of therapeutic monoclonal antibodies. FEBS Lett 2014; 588:308-17.
18. Leurs U, Mistarz U H, Rand K D. Getting to the core of protein pharmaceuticals—Comprehensive structure analysis by mass spectrometry. Eur J Pharm Biopharm Off J Arbeitsgemeinschaft Far Pharm Verfahrenstechnik EV 2015; 93:95-109.
19. Jardine I. Electrospray ionization mass spectrometry of biomolecules. Nature 1990; 345:747-8.
20. Loo J A. Electrospray ionization mass spectrometry: a technology for studying noncovalent macromolecular complexes. Int J Mass Spectrom 200:175-86.
21. Deng B, Lento C, Wilson D J. Hydrogen deuterium exchange mass spectrometry in biopharmaceutical discovery and development—A review. Anal Chim Acta 2016; 940:8-20.
22. Pirrone G F, Iacob R E, Engen J R. Applications of hydrogen/deuterium exchange MS from 2012 to 2014. Anal Chem 2015; 87:99-118.
23. Zhang Z, Smith D L. Determination of amide hydrogen exchange by mass spectrometry: a new tool for protein structure elucidation. Protein Sci Publ Protein Soc 1993; 2:522-31.
24. Konermann L, Pan J, Liu Y-H. Hydrogen exchange mass spectrometry for studying protein structure and dynamics. Chem Soc Rev 2011; 40:1224-34.
25. Englander J J, Del Mar C, Li W, Englander S W, Kim J S, Stranz D D, Hamuro Y, Woods V L. Protein structure change studied by hydrogen-deuterium exchange, functional labeling, and mass spectrometry. Proc Natl Acad Sci USA 2003; 100:7057-62.
26. Hager-Braun C, Tomer K B. Determination of protein-derived epitopes by mass spectrometry. Expert Rev Proteomics 2005; 2:745-56.
27. Konermann L. Heavy lessons in protein allostery. Nat Struct Mol Biol 2016; 23:511-2.
28. Resetca D, Wilson D J. Characterizing rapid, activity-linked conformational transitions in proteins via sub-second hydrogen deuterium exchange mass spectrometry. FEBS J 2013; 280:5616-25.
29. Resetca D, Haftchenary S, Gunning P T, Wilson D J. Changes in signal transducer and activator of transcription 3 (STAT3) dynamics induced by complexation with pharmacological inhibitors of Src homology 2 (SH2) domain dimerization. J Biol Chem 2014; 289:32538-47.
30. Zhu S, Shala A, Bezginov A, Sljoka A, Audette G, Wilson D J. Hyperphosphorylation of intrinsically disordered tau protein induces an amyloidogenic shift in its conformational ensemble. PloS One 2015; 10:e0120416.

31. Rob T, Liuni P, Gill P K, Zhu S, Balachandran N, Berti P J, Wilson D J. Measuring dynamics in weakly structured regions of proteins using microfluidics-enabled subsecond H/D exchange mass spectrometry. Anal Chem 2012; 84:3771-9.
32. Wilson D J, Konermann L. A capillary mixer with adjustable reaction chamber volume for millisecond time-resolved studies by electrospray mass spectrometry. Anal Chem 2003; 75:6408-14.
33. Wales T E, Fadgen K E, Gerhardt G C, Engen J R. High-speed and high-resolution UPLC separation at zero degrees Celsius. Anal Chem 2008; 80:6815-20.
34. Anti-Myoglobin antibody [EP3081Y] (ab77232)|Abcam product information: http://www.abcam.com/myoglobin-antibody-ep3081y-ab77232.html
35. Atassi M Z. Antigenic structure of myoglobin: the complete immunochemical anatomy of a protein and conclusions relating to antigenic structures of proteins. Immunochemistry 1975; 12:423-38.
36. Rob T, Gill P K, Golemi-Kotra D, Wilson D J. An electrospray ms-coupled microfluidic device for sub-second hydrogen/deuterium exchange pulse-labelling reveals allosteric effects in enzyme inhibition. Lab Chip 2013; 13:2528-32.
37. Whiteley W. Counting out to the flexibility of molecules. Phys Biol 2005; 2:S116-126.
38. Jacobs D J, Rader A J, Kuhn L A, Thorpe M F. Protein flexibility predictions using graph theory. Proteins 2001; 44:150-65.
39. Kim T H, Mehrabi P, Ren Z, Sljoka A, Ing C, Bezginov A, Ye L, Pornes R, Prosser R S, Pai E F. The role of dimer asymmetry and protomer dynamics in enzyme catalysis. Science 2017; 355:eaag2355.
40. Sowole M A, Simpson S, Skovpen Y V, Palmer D R J, Konermann L. Evidence of Allosteric Enzyme Regulation via Changes in Conformational Dynamics: A Hydrogen/Deuterium Exchange Investigation of Dihydrodipicolinate Synthase. Biochemistry (Mosc) 2016; 55:5413-22.
41. Laskowski R A, Gerick F, Thornton J M. The structural basis of allosteric regulation in proteins. FEBS Lett 2009; 583:1692-8.
42. Hacisuleyman A, Erman B. Entropy Transfer between Residue Pairs and Allostery in Proteins: Quantifying Allosteric Communication in Ubiquitin. Plos Comput Biol 2017; 13:e1005319.
43. Ceruso M A, Periole X, Weinstein H. Molecular dynamics simulations of transducin: interdomain and front to back communication in activation and nucleotide exchange. J Mol Biol 2004; 338:469-81.
44. Popovych N, Sun S, Ebright R H, Kalodimos C G. Dynamically driven protein allostery. Nat Struct Mol Biol 2006; 13:831-8.
45. Taraska J W, Zagotta W N. Structural dynamics in the gating ring of cyclic nucleotide-gated ion channels. Nat Struct Mol Biol 2007; 14:854-60.
46. Li J, Callaway D J E, Bu Z. Ezrin Induces Long-Range Interdomain Allostery in the Scaffolding Protein NHERF1. J Mol Biol 2009; 392:166-80.
47. Molecular Operating Environment (MOE), 2013.08; Chemical Computing Group Inc., 1010 Sherbooke St. West, Suite #910, Montreal, QC, Canada, H3A 2R7, 2016.
48. Pierce B G, Wiehe K, Hwang H, Kim B-H, Vreven T, Weng Z. ZDOCK server: interactive docking prediction of protein-protein complexes and symmetric multimers. Bioinforma Oxf Engl 2014; 30:1771-3.
49. Mashiach E, Schneidman-Duhovny D, Peri A, Shavit Y, Nussinov R, Wolfson H J. An integrated suite of fast docking algorithms. Proteins 2010; 78:3197-204.

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A time-resolved electrospray ionization mass spectrometry with hydrogen deuterium exchange (TRESI-HDX)-based method for mapping protein-protein interactions, the method comprising substantially simultaneously (a) initiating complexation between the proteins and (b) labelling the complex, wherein the labelling time is about 200 ms and wherein transfer from labeling to ionization is under quench conditions and takes less than about 10 s.

2. The method of claim 1, wherein the proteins comprise an antibody and an antigen, an enzyme and a substrate, or a drug and a drug target.

3. The method of claim 1, wherein transfer from labeling to ionization takes less than about 4 s.

4. The method of claim 1, further comprising mass spectrometry (MS) detection and data analysis.

5. The method of claim 1, wherein the method further comprises allowing for an hydrogen deuterium exchange (HDX) signal to develop as allostery is propagated after a binding event, thereby distinguishing between binding and allostery.

6. The method of claim 5, further comprising mass spectrometry (MS) detection and data analysis.

7. A method of epitope mapping, wherein the method comprises introducing an antibody to an antigen through a time-resolved electrospray ionization (TRESI) mixer so that binding and labeling are initiated substantially simultaneously, wherein the labelling time is about 200 ms, and wherein transfer from labeling to ionization is under quench conditions and takes less than about 10 s.

8. The method of claim 7, wherein the TRESI mixer comprises a time-resolved electrospray ionization mass spectrometry with hydrogen deuterium exchange TRESI-HDX chip comprising laminar-flow disturbing microstructures after acid-quenching channels for improving mixing between a deuterated protein and a quench solution.

9. The method of claim 8, wherein transfer from labeling to ionization takes less than about 4 s.

10. The method of claim 7, further comprising mass spectrometry (MS) detection and data analysis.

* * * * *

UNITED STATES PATENT AND TRADEMARK OFFICE
CERTIFICATE OF CORRECTION

PATENT NO. : 11,061,036 B2
APPLICATION NO. : 16/132925
DATED : July 13, 2021
INVENTOR(S) : Wilson et al.

Page 1 of 1

It is certified that error appears in the above-identified patent and that said Letters Patent is hereby corrected as shown below:

In the Specification

Column 7, Line 41: Please correct "labor intensive:$^{16}$" to read -- labor intensive.$^{16}$ --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*